United States Patent [19]

Porat et al.

[11] Patent Number: 4,727,876

[45] Date of Patent: Mar. 1, 1988

[54] MEDICAL FORCEPS OR CLAMPS

[76] Inventors: Michael Porat; Amir Porat, both of 2 Kufman St., P.O.B. 50355, Tel Aviv 61500, Israel

[21] Appl. No.: 704,335

[22] Filed: Feb. 22, 1985

[30] Foreign Application Priority Data

Sep. 26, 1984 [IL] Israel .......................................... 73078

[51] Int. Cl.⁴ ............................................... A61B 17/30
[52] U.S. Cl. ...................................... 128/354; 433/159
[58] Field of Search ................ 128/354, 351, 314, 335, 128/334, 334 C, 321; 433/159

[56] References Cited

U.S. PATENT DOCUMENTS

| | | | |
|---|---|---|---|
| 2,674,800 | 4/1954 | Osborn et al. | 433/159 |
| 3,265,068 | 8/1966 | Holohan | 128/354 |
| 3,367,336 | 2/1968 | Eizenberg | 128/354 |
| 4,096,864 | 6/1978 | Kletschka | 128/354 |
| 4,462,404 | 7/1984 | Schwarz et al. | 128/354 |

Primary Examiner—Gene Mancene
Assistant Examiner—Wenceslao J. Contreras
Attorney, Agent, or Firm—Abelman Frayne Rezac & Schwab

[57] ABSTRACT

A medical forceps having a core of metal, a molded-on layer of plastics in sandwich-like manner. In particular, medical forceps wherein the part of the core which is destined to become the gripping part is covered by a plastic gripping means with or without teeth.

3 Claims, 4 Drawing Figures

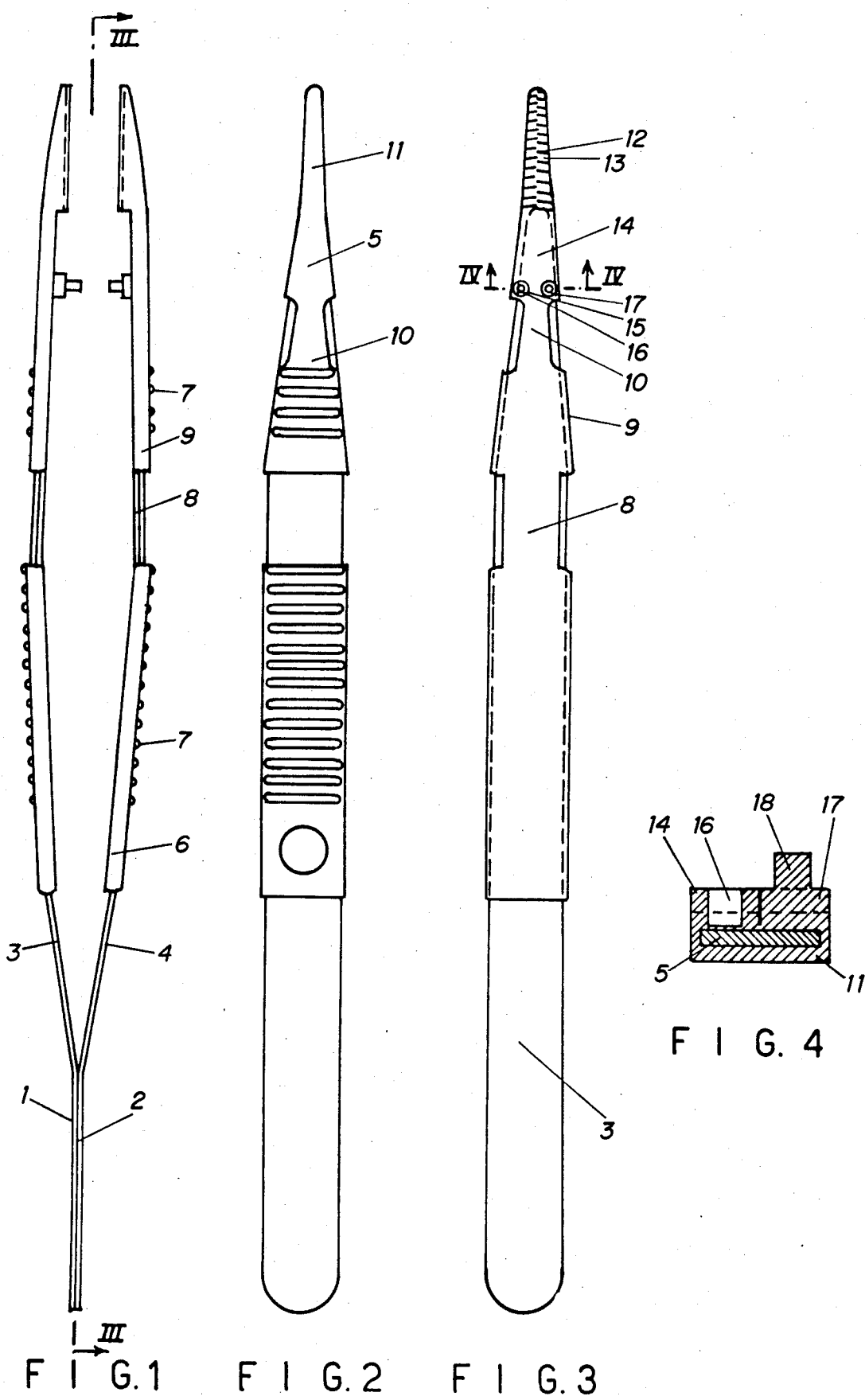

MEDICAL FORCEPS OR CLAMPS

The present invention concerns forceps used in medicine, hereinafter collectively referred to as forceps.

Forceps made of metal are known and their manufacture is generally costly since the part which performs the gripping action has to be finished by hand. If these forceps are mass-produced their quality is generally inferior especially as far as accuracy of the gripping part is concerned which must contain grooves and teeth in order to able to grip veins, delicate threads, hair, body tissue and the line.

There are known plastic forceps which have been produced to overcome the disadvantages of the metal ones, since the teeth and grooves of the gripping parts can be manufactured accurately by molding. However, these forceps are not very strong and are liable to bend during use.

There are known scissors in which the cutting part is made of metal, while the handles are either of plastics entirely or are of metal coated with plastics. The plastic coating here is for convenience only. There are further known medical scissors-like clamps in which the fingergrips only are made of plastic, the metal gripping parts being inserted therein.

It is the object of the present invention to provide a forceps which combines the advantages of both metal and plastic ones i.e. the elasticity of the metal and the possibility of the plastics to achieve high accuracy when molded.

The invention consists in a medical forceps having a core of metal, its gripping members being at least partially covered by a molded-on layer of plastics in sandwich-like manner.

The invention is illustrated by way of example only in the accompanying drawing in which:

FIG. 1 is a plan view of the medical forceps according to the invention.

FIG. 2 is a side elevation thereof.

FIG. 3 is a section taken on line III—III of FIG. 2.

FIG. 4 is a section taken on line IV—IV of FIG. 3.

The forceps according to the invention comprises a metal core 1 in the shape of the known forceps, i.e. the handle part 2 and the gripping members 3 and 4, having the gripping part 5 which is without the teeth and grooves. The gripping members 3 and 4 are covered in sandwich-like manner by a plastic molded-on covering which envelopes them at the stretch 6 close to the handle part 2, the stretch 6 being smooth on the inside and having ribs 7 on the outside to facilitate grasping when the forceps are held in the hand. A first bridge member 8 merges with stretch 6 only on the inside of the gripping member, a second stretch 9 having ribs 7 on the outside merging with bridge member 8 and surrounds the core part. A second bridge member 10 merges with stretch 9 both on the inside and the outside, the gripping part 11 which is of increased thickness and evelopes the gripping part 5, being smooth on the outside and having teeth 12 and grooves 13 on the inside merging with bridge member 10. The teeth 12 and grooves 13 extend at the same angle on either side of an imaginary longitudinal median line 14. The row of teeth 12 which lies on one side of line 14 is staggered in relationship to those on the other side of said line, as described and claimed in our co-pending patent application. Adjacent to bridge member 10 guide means are provided which comprise on one side of line 14 an integral cylinder 15 in which a depression 16 is provided and on the other side of said line 14 an integral cylinder 17 from which a short pin 18 extends upwardly, the diameter of pin 18 corresponding substantially to that of depression 16. Thus when the two gripping members of one pair of forceps face each other the teeth 12 of one row will engage in the interstices 13 of the other row and pin 18 will engage in depression 16 of the opposite gripping member. Owing to this construction, forceps having strength and excellent accuracy are provided while the elasticity of the metal is retained to provide good gripping action.

It can be seen that the forceps can be mass-produced by making two identical parts which can be welded together at the handle part, since it is without a plastic covering. In this manner the costs of the forceps are minimal.

If desired, the plastic covering may be over the entire core of the forceps, or may be over a part of the core which is less than that above described. Furthermore, the forceps may be provided with a gripping part without teeth and grooves.

We claim:

1. A medical forceps defining a handle from which extend two integral gripping members and comprising a core of metal and wherein the metal core of said gripping members is at least partially covered by a molded-on layer of plastics material in a sandwich-like manner, said layer of plastics being shaped to define the gripping members, wherein guiding means are provided on the plastic gripping members on both sides of a longitudinal median line, comprising on one side of said line a cylinder having a depression and, on the other, a cylinder from which a pin extends, the diameter of the pin corresponding substantially to that of the depression.

2. A medical forceps as claimed in claim 1, wherein each gripping member is made separately, and two such members are welded together at their handle parts which are bare of a plastic covering.

3. A medical forceps or clamps as claimed in claim 1, wherein the parts destined to be held in the hand are of plastics.

* * * * *